(12) United States Patent
Yoshimura et al.

(10) Patent No.: US 10,441,535 B2
(45) Date of Patent: Oct. 15, 2019

(54) NUTRACEUTICAL CONFECTIONARY COMPOSITION CONTAINING CAFFEINE AND L-THEANINE

(71) Applicant: NeuroGum, LLC, Los Angeles, CA (US)

(72) Inventors: Kent Yoshimura, Los Angeles, CA (US); Ryan Chen, Los Angeles, CA (US)

(73) Assignee: NEUROGUM, LLC, Los Angeles, CA (US)

( * ) Notice: Subject to any disclaimer, the term of this patent is extended or adjusted under 35 U.S.C. 154(b) by 0 days.

(21) Appl. No.: 14/975,753

(22) Filed: Dec. 19, 2015

(65) Prior Publication Data

US 2016/0303042 A1   Oct. 20, 2016

(51) Int. Cl.
| | |
|---|---|
| A61K 9/68 | (2006.01) |
| A61K 31/198 | (2006.01) |
| A61K 31/522 | (2006.01) |
| A23G 4/06 | (2006.01) |
| A23G 4/12 | (2006.01) |
| A23G 4/14 | (2006.01) |
| A23L 33/105 | (2016.01) |
| A23L 33/175 | (2016.01) |
| A61K 9/20 | (2006.01) |

(52) U.S. Cl.
CPC ............ *A61K 9/0058* (2013.01); *A23G 4/068* (2013.01); *A23G 4/14* (2013.01); *A23L 33/105* (2016.08); *A23L 33/175* (2016.08); *A61K 9/2086* (2013.01); *A61K 9/2095* (2013.01); *A61K 31/198* (2013.01); *A61K 31/522* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 5,501,866 A * | 3/1996 | Kakuda | A23F 3/363 |
| | | | 426/594 |
| 6,024,988 A | 2/2000 | Ream et al. | |
| 7,232,581 B2 | 6/2007 | Mikkelsen et al. | |
| 7,521,074 B2 | 4/2009 | Mikkelsen et al. | |
| 8,137,716 B2 | 3/2012 | Mikkelsen et al. | |
| 8,329,235 B2 | 12/2012 | Mikkelsen et al. | |
| 8,636,985 B2 | 1/2014 | Barron | |
| 2004/0180007 A1* | 9/2004 | Ream | A23G 3/343 |
| | | | 424/48 |
| 2005/0220934 A1* | 10/2005 | Leadbeater | A23G 4/00 |
| | | | 426/3 |
| 2005/0287278 A1* | 12/2005 | Quan | A23F 3/18 |
| | | | 426/597 |
| 2006/0034897 A1* | 2/2006 | Boghani | A23G 3/0017 |
| | | | 424/440 |
| 2006/0159829 A1* | 7/2006 | Owen | A23F 3/14 |
| | | | 426/597 |
| 2008/0260899 A1* | 10/2008 | Schmidt | A23G 4/20 |
| | | | 426/4 |
| 2010/0255063 A1* | 10/2010 | Andersen | A61K 9/0058 |
| | | | 424/440 |
| 2012/0121520 A1* | 5/2012 | Barron | A61K 9/0058 |
| | | | 424/48 |
| 2013/0052234 A1* | 2/2013 | Goldberg | A61K 9/0056 |
| | | | 424/400 |

FOREIGN PATENT DOCUMENTS

| | | | |
|---|---|---|---|
| CN | 1868296 A | * 11/2006 | |
| WO | WO-2006063189 A2 | * 6/2006 | ............ A61K 9/0056 |

OTHER PUBLICATIONS

Bryan, Janet. "Psychological effects of dietary components of tea: caffeine and L-theanine." Nutrition reviews 66.2 (2008):82-90.*
John J. Foxe, Kristen P. Morie, Peter J. Laud, Matthew J. Rowson, Eveline A. de Bruin, Simon P. Kelly. Assessing the effects of caffeine and theanine on the maintenance of vigilance during a sustained attention task. Neuropharmacology 62 (2012), pp. 2320-2327.*
Birgitte Hyrup, Carsten Andersen, Lars Vibe Andreasen, Bo Tandrup, and Torben Christensen. The MediChew® technology platform. Expert Opin. Drug Deliv. (2005) 2(5): 927-933.*
English translation of CH1868296A provided by EPO/Google.*
Entry for "Theanine" in Wikipedia (accessed Apr. 26, 2017 from: https://en.wikipedia.org/wiki/Theanine).*
Definition of "may" as "Used to express possibility or probability", as per the evidentiary reference of the Free Dictionary Online, downloaded Apr. 27, 2017 from http://www.thefreedictionary.com/ May.*
Shivang a Chaudhary & Aliasgar F Shahiwala. Medicated chewing gum—a potential drug delivery system. Expert Opin. Drug Deliv . (2010) 7(7): 871-885. (Year: 2010).*
Smith, Andrew, Effects of chewing gum on mood, learning, memory and performance of an intelligence test. Nutritional Neuroscience, Apr. 2009; 12(2):81-8.

(Continued)

*Primary Examiner* — Michael P Cohen
(74) *Attorney, Agent, or Firm* — Kwan & Olynick LLP

(57) ABSTRACT

In general, certain embodiments of the present disclosure provide compositions or mechanisms for oral administration of caffeine via a functional nutraceutical confectionary composition. According to various embodiments, a nutraceutical confectionary composition is provided with a ratio of caffeine to L-theanine ranging from about 1:1 to about 1:2. In some embodiments, the ratio of caffeine to L-theanine is about 2:3. In various embodiments, the nutraceutical confectionary composition may provide caffeine in a range from about 5 mg to about 100 mg per serving. L-theanine may be provided in a range from about 5 mg to about 200 mg per serving. In some embodiments, caffeine may comprise about 0.8% to 10% by weight of the composition; and L-theanine may comprise about 1.2% to 20% by weight of the composition. In certain embodiments, the nutraceutical confectionary composition may comprise a chewing gum.

5 Claims, 11 Drawing Sheets

(56) References Cited

OTHER PUBLICATIONS

AC Nobre, et al., L-theanine, a natural constituent in tea, and its effect on mental state. Asia Pacific Journal Clinical Nutrition 2008; 17 Suppl 1: 167-8.

Szilagyi, G., et al., Effects of vinpocetine on the redistribution of cerebral blood flow and glucose metabolism in chronic ischemic stroke patients: a PET study, Abstract. Journal of the Neurological Sciences. Mar. 15, 2005; 229-230:275-84.

Dezsi, L., et al., Neuroprotective effects of vinpocetine in vivo and in vitro. Apovincaminic acid derivatives as potential therapeutic tools in ischemic stroke, English Abstract. Acta Pharmaceutica Hungarica. 2002; 72(2):84-91, Hungary.

Shende, Pravin, et al., Multi-layer Tablet: Current scenario and recent advances. International Journal of Drug Delivery. 2012; 4(4):418-426.

Nilawar, Priyal S., et al., An Emerging Trend on Bilayer Tablets. International Journal of Pharmacy and Pharmaceutical Science Research 2013; 3(1):15-21.

Gopinath, C., et al., An Overview on Bilayered Tablet Technology. Journal of Global Trends in Pharmaceutical Sciences. 2013; 4(2):1077-1085.

Van Der Pijl, P.C., et al., Human disposition of L-theanine in tea or aqueous solution. Journal of Functional Foods. 2010; 2(4):239-244.

Scheid, Lisa, et al., Kinetics of L-Theanine Uptake and Metabolism in Healthy Participants Are Comparable After Ingestion of L-Theanine via Capsules and Green Tea. The Journal of Nutrition. Dec. 2012; 142(12):2091-6.

Syed, Shariq A., et al., Multiple Dose Pharmacokinetics of Caffeine Administered in Chewing Gum to Normal Healthy Volunteers. Biopharmaceutics & Drug Disposition. Dec. 2005;26(9):403-9.

Scott, N.R. et al., The pharmacokinetics of caffeine and its dimethylxanthine metabolites in patients with chronic liver disease. Br J Clin Pharmacol. Feb. 1989; 27(2): 205-213.

Kamimori, Gary H., et al., The rate of absorption and relative bioavailability of caffeine administered in chewing gum versus capsules to normal healthy volunteers. International Journal of Pharmaceutics. Mar. 2, 2002;234(1-2):159-67.

* cited by examiner

Caffeine ($C_8H_{10}N_4O_2$)

L-Theanine ($C_7H_{14}N_2O_3$)

NUTRACEUTICAL CONFECTIONARY COMPOSITION CONTAINING CAFFEINE AND L-THEANINE

TECHNICAL FIELD

The present disclosure relates generally to nutraceutical confectionaries, and more specifically to chewing gum containing nutraceutical agents.

BACKGROUND

Caffeine is a xanthine alkaloid, and a cardiac and mental stimulant typically sourced from tea leaves or coffee beans. Caffeine is one of the most widely used stimulants throughout the world and consumed in various forms such as coffee tea, energy drinks and many others. In humans, it stimulates the central nervous system and temporarily reduces fatigue and restores alertness by binding to the adenosine receptors in nerve cells. Consumption of beverages and food items containing caffeine has been shown to improve specific aspects of memory, performance, and attention. However, consumption of caffeine may have negative effects on the body, including increased anxiety and disruption of sleep patterns. Other possible negative side effects include nausea, restlessness, tremors, and vomiting. Drinking coffee may also cause halitosis and stained teeth. Thus, there is a need for an improved method for administering caffeine in an individual quickly while eliminating or reducing its negative effects.

SUMMARY

The following presents a simplified summary of the disclosure in order to provide a basic understanding of certain embodiments of the present disclosure. This summary is not an extensive overview of the disclosure and it does not identify key/critical elements of the present disclosure or delineate the scope of the present disclosure. Its sole purpose is to present some concepts disclosed herein in a simplified form as a prelude to the more detailed description that is presented later.

In general, certain embodiments of the present disclosure provide compositions or mechanisms for oral administration of caffeine via a functional nutraceutical confectionary composition. According to various embodiments, a nutraceutical confectionary composition is provided. The nutraceutical confectionary comprises caffeine and L-theanine in combination with a nutraceutically acceptable carrier. According to various embodiments, the ratio of caffeine to L-theanine may range from about 1:1 to about 1:2. In some embodiments, the ratio of caffeine to L-theanine may range from about 3:5 to about 4:5. In other embodiments, the ratio of caffeine to L-theanine is about 2:3. In various embodiments, the nutraceutical confectionary composition may provide caffeine in a range from about 5 mg to about 100 mg per serving. L-theanine may be provided in a range from about 5 mg to about 200 mg per serving. In another embodiment, the nutraceutical confectionary composition may comprise about 40 mg to about 60 mg of caffeine per serving and about 40 mg to about 120 mg of L-theanine per serving. In some embodiments, caffeine may comprise about 0.8% to 10% by weight of the composition; and L-theanine may comprise about 1.2% to 20% by weight of the composition.

In some embodiments, the nutraceutical confectionary composition may comprise a chewing gum. In other embodiments, the chewing gum may comprise caffeine in an amount from about 40 mg to about 100 mg; L-theanine in an amount from about 40 mg to about 200 mg, gum base in an amount from about 600-700 mg; natural flavors in an amount from about 20 mg to about 100 mg; and calcium stearate in an amount from about 20 mg to about 50 mg.

In some embodiments, the chewing gum may further comprise a tablet manufactured by a process that comprises providing a powdered gum base and combining caffeine in a range from about 10 mg to about 30 mg per serving, and L-theanine in a range from about 30 mg to about 50 mg per serving, by mixing with the powdered gum base to form a first mixture. The process may further comprise providing a powdered mixture comprising a binding agent and a sweetener, and combining caffeine in a range from about 5 mg to about 15 mg per serving, and L-theanine in a range from about 5 mg to about 15 mg per serving, by mixing with the powdered mixture to form a second mixture. A serving of the first mixture is then added into a die in a tablet compression system and compressed into a first layer of the tablet. A serving of the second mixture is then loaded into the die onto the first layer. The process may further comprise compressing the serving of the second mixture and the first layer such that the serving of the second mixture becomes a second layer of the tablet coupled to the first layer. The tablet may then be ejected from the die.

In other embodiments, the nutraceutical confectionary composition may further comprise a combination of one or more vitamins or minerals. In further embodiments, the nutraceutical confectionary composition may further comprise a probiotic strain.

In yet another implementation, a method for treating an individual for increasing energy and alertness while maintaining relaxation and focus is provided. The method comprises orally administering to an individual a nutraceutical confectionary composition comprising caffeine and L-theanine in combination with a nutraceutically acceptable carrier such that the caffeine and L-theanine are absorbed through the individual's oral mucosa. According to various embodiments, the ratio of caffeine to L-theanine may range from about 1:1 to about 1:2. In some embodiments, the ratio of caffeine to L-theanine may range from about 3:5 to about 4:5. In other embodiments, the ratio of caffeine to L-theanine is about 2:3. In various embodiments, the nutraceutical confectionary composition may provide caffeine in a range from about 5 mg to about 100 mg per serving. L-theanine may be provided in a range from about 5 mg to about 200 mg per serving. In another embodiment, the nutraceutical confectionary composition may comprise about 40 mg to about 60 mg of caffeine per serving and about 40 mg to about 120 mg of L-theanine per serving. In some embodiments, caffeine may comprise about 0.8% to 10% by weight of the composition; and L-theanine may comprise about 1.2% to 20% by weight of the composition.

In some embodiments, the nutraceutical confectionary composition may comprise a chewing gum. In some embodiments, chewing of the chewing gum by the individual causes the caffeine and L-theanine to be released into the individual's oral cavity. In other embodiments, the chewing gum may further comprise caffeine in an amount from about 40 mg to about 100 mg; L-theanine in an amount from about 40 mg to about 200 mg; gum base in an amount from about 600-700 mg; natural flavors in an amount from about 20 mg to about 100 mg; and calcium stearate in an amount from about 20 mg to about 50 mg. In some embodiments, the nutraceutical confectionary composition may further comprise a combination of one or more vitamins or minerals.

BRIEF DESCRIPTION OF THE DRAWINGS

The disclosure may best be understood by reference to the following description taken in conjunction with the accompanying drawings, which illustrate particular embodiments of the present disclosure.

DESCRIPTION OF PARTICULAR EMBODIMENTS

Figure 1:
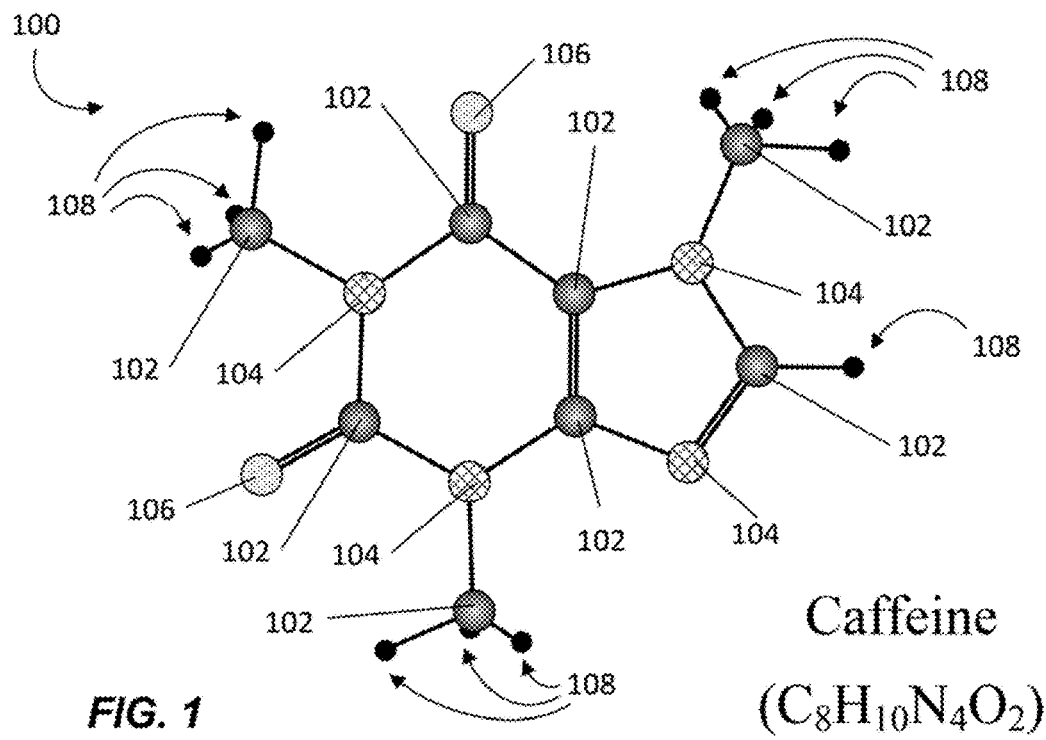
FIG. 1 is an illustration of an example of a caffeine molecule that may be used in conjunction with the methods and compositions of the present disclosure, in accordance with one or more embodiments.

Reference will now be made in detail to some specific examples of the present disclosure including the best modes contemplated by the inventors for carrying out the present disclosure. Examples of these specific embodiments are illustrated in the accompanying drawings. While the present disclosure is described in conjunction with these specific embodiments, it will be understood that it is not intended to limit the present disclosure to the described embodiments. On the contrary, it is intended to cover alternatives, modifications, and equivalents as may be included within the spirit and scope of the present disclosure as defined by the appended claims.

For example, the techniques and mechanisms of the present disclosure will be described in the context of particular confectionaries. However, it should be noted that the techniques and mechanisms of the present disclosure apply to a variety of edibles. In the following description, numerous specific details are set forth in order to provide a thorough understanding of the present disclosure. Particular example embodiments of the present disclosure may be implemented without some or all of these specific details.

As used herein, the terms "user," "individual," "subject," and "person" are used interchangeably to refer to one being administered a nutraceutical confectionary composition.

Various techniques and mechanisms of the present disclosure will sometimes be described in singular form for clarity. However, it should be noted that some embodiments include multiple iterations of a technique or multiple instantiations of a mechanism unless noted otherwise. For example, a confectionary may include a variety of flavors or layers of different ingredients. However, it will be appreciated that a confectionary can contain multiple layers of different flavors and ingredients while remaining within the scope of the present disclosure unless otherwise noted.

Overview

According to various embodiments, a nutraceutical confectionary composition is provided. The nutraceutical confectionary comprises caffeine and L-theanine in combination with a nutraceutically acceptable carrier. In yet another implementation, a method for treating an individual for increasing energy and alertness while maintaining relaxation and focus is provided. The method comprises orally administering to an individual a nutraceutical confectionary composition comprising caffeine and L-theanine in combination with a nutraceutically acceptable carrier such that the caffeine and L-theanine are absorbed through the individual's oral mucosa.

According to various embodiments, the ratio of caffeine to L-theanine may range from about 1:1 to about 1:2. In some embodiments, the ratio of caffeine to L-theanine may range from about 3:5 to about 4:5. In other embodiments, the ratio of caffeine to L-theanine is about 2:3. In various embodiments, the nutraceutical confectionary composition may provide caffeine in a range from about 5 mg to about 100 mg per serving. L-theanine may be provided in a range from about 5 mg to about 200 mg per serving. In another embodiment, the nutraceutical confectionary composition may comprise about 40 mg to about 60 mg of caffeine per serving and about 40 mg to about 120 mg of L-theanine per serving. In some embodiments, caffeine may comprise about 0.8% to 10% by weight of the composition; and L-theanine may comprise about 1.2% to 20% by weight of the composition. In certain embodiments, the nutraceutical confectionary composition may comprise a chewing gum.

Example Embodiments

According to various embodiments, a confectionary may include one or more nootropic agents, including, but not limited to, stimulants, nutraceuticals, and racetams. In other embodiments, the confectionary may additionally, or alternatively, include various vitamins or other dietary supplements. In some embodiments, the confectionary may comprise a chewing gum. In other embodiments, the confectionary may comprise other edible food items such as mints, hard candy, soft candy, dissolvable strips, baked goods, etc.

In some embodiments, the confectionary may include a combination of effective amounts of caffeine and L-theanine with a nutraceutically acceptable carrier. Caffeine is a crystalline xanthine alkaloid that acts as a stimulant for the metabolic system and the central nervous system. Conventionally, caffeine is used to reduce physical fatigue and improve awareness and alertness. Although the effect of caffeine is different for each user, caffeine may also contribute to keeping users awake despite sleep deprivation conditions. L-theanine is a non-protein amino acid primarily found in both green and black tea. L-theanine has been shown to cause a calm but alert, focused, and relatively productive (alpha wave dominant) mental state in humans.

When combined, L-theanine and caffeine result in synergistic effects in cognition and mood.

In some embodiments, the advantageous effects are achieved by combining the caffeine and L-theanine with a nutraceutically acceptable carrier in a sublingual formulation, or some other delivery system that may be rapidly absorbed by the oral mucosa. One useful sublingual functional food delivery system may comprise confectionaries, such as chewing gum. Other similar functional food delivery systems may include, but are not limited to, dissolvable tabs placed under the tongue and/or at the cheeks, oral dissolvable films or dissolvable strips, liquid drops, and lozenges. As used herein, a "nutraceutically acceptable carrier" refers to any carrier, dilutent, or excipient that is compatible with the other active or inactive ingredients of the formulation and not harmful to the user. In various embodiments, a nutraceutically acceptable carrier may comprise one or more binders, excipients, buffers, and flavoring agents. For example, in an embodiment where the nutraceutical confectionary comprises a chewing gum, such nutraceutically acceptable carrier may comprise a suitable gum base mixture. In various embodiments, such gum base mixture may be provided in powdered form and combined with other active and inactive ingredients as further described in conjunction with FIGS. 3A, 3B, and 3C below. In other embodiments, such a nutraceutically acceptable carrier may comprise stabilizing agents, such as calcium stearate, or other sweeteners, such as sorbitol, steviol glycosides, and acesulfame potassium. In various embodiments such ingredients may be provided in powdered form and combined with other active and inactive ingredients as further described in conjunction with FIGS. 3A, 3B, and 3C below.

In some embodiments, a chewing gum may include caffeine and L-theanine in an ideal ratio to optimize the synergistic effects of the compounds. For example, the chewing gum may include caffeine and L-theanine in about a 1:1 ratio. In other embodiments, the chewing gum may include increased amounts of L-theanine such that the ratio of L-theanine to caffeine may rise to about 2:1 in the chewing gum. In another embodiment, the chewing gum may comprise a 2:3 ratio of caffeine to L-theanine. In some embodiments, a chewing gum may contain about 40 mg of caffeine and 60 mg of L-theanine, 40 mg of caffeine is approximately the one half of the amount of caffeine found in an ordinary cup of coffee. In other embodiments, the amount of caffeine in the chewing gum may range from 5 mg per serving to 100 mg per serving. In some embodiments, the amount of L-theanine in the chewing gum may range from 5 mg per serving to 200 mg per serving.

In various embodiments, the chewing gum may be a tablet ranging in weight from about 1 gram to about 5 grams. In some embodiments, the amount of caffeine may comprise from about 0.8% to about 10% by weight of the composition. In some embodiments, the amount of L-theanine may comprise from about 1.2% to about 20% by weight of the composition. In some embodiments, the gum may contain various flavoring agents including, but not limited to, the following flavors: ginger, tropical, fruit, berry, mint, spearmint, and cinnamon.

In some embodiments, mastication of the chewing gum by a user may release the active nutraceutical agents, such as caffeine and L-theanine into the user's saliva. The active nutraceutical agents may dissolve in the user's saliva and be absorbed by the sublingual or buccal areas of the user's mouth. In some embodiments, the active nutraceutical agents in saliva may be swallowed and may further be absorbed in the user's digestive tract.

In various embodiments sublingual and/or buccal administration allows for quick absorption by the oral mucosa for more immediate effects. Because, the active nutraceutical agents do not have to pass through the digestive system where they may be denatured by digestive enzymes or metabolized by the liver, sublingual and/or buccal administration allows for a more precise dosage of active nutraceutical agents, as well as a lower amount to be used in the confectionary. In other embodiments, administration through sublingual and/or buccal absorption may avoid other negative effects caused by drinking coffee, such as stained teeth, halitosis, and other gastrointestinal issues. In further embodiments, the chewing action may also increase alertness and concentration, which can further complement the beneficial effects of the active nootropic agents previously described above.

In accordance with various embodiments, the chewing gum may be manufactured through a cold compression process. A gum composition produced by cold compression allows for the greatest consistency of functional ingredients in each piece of gum. In contrast to the traditional extruded gum manufacturing process, a cold compression process does not use heat or moisture during manufacturing which ensures that substantially no active nutraceutical ingredients are lost in manufacturing, and may allow about 100% of active ingredients to be released during consumption.

The nutraceutical composition and methods described above may be further understood in connection with the following Figures and Examples.

FIG. 1 is an illustration of an example of a caffeine molecule 100 that may be used in conjunction with the methods and compositions of the present disclosure, in accordance with one or more embodiments. Caffeine molecule 100 has a molecular formula of $C_8H_{10}N_4O_2$ and includes eight Carbon atoms 102, four Nitrogen atoms 104, two Oxygen atoms 106, and ten Hydrogen atoms 108. Caffeine 100 is a crystalline xanthine alkaloid that works as a stimulant in humans to temporarily reduce physical fatigue, prevent drowsiness, and restore alertness. In some embodiments, caffeine molecule 100 may be provided as caffeine anhydrous containing 0.5% or less water. In other embodiments, caffeine 100 may be provided in various other forms from various other sources.

In humans, caffeine produces increased wakefulness, improved through-processing, increased focus, and better general body coordination by, among other things, reversibly blocking the action of adenosine on adenosine receptors, stimulating certain portions of the autonomic nervous systems, and increasing blood pressure. In addition to such desired stimulating effects, intake of caffeine may also cause negative side effects such as increased anxiety, restlessness, disruption of sleep patterns, headaches, nausea, tremors, vomiting, etc. Consumption of coffee, a popular source of caffeine, may also cause halitosis, stained teeth, and other gastrointestinal issues.

Figure 2:
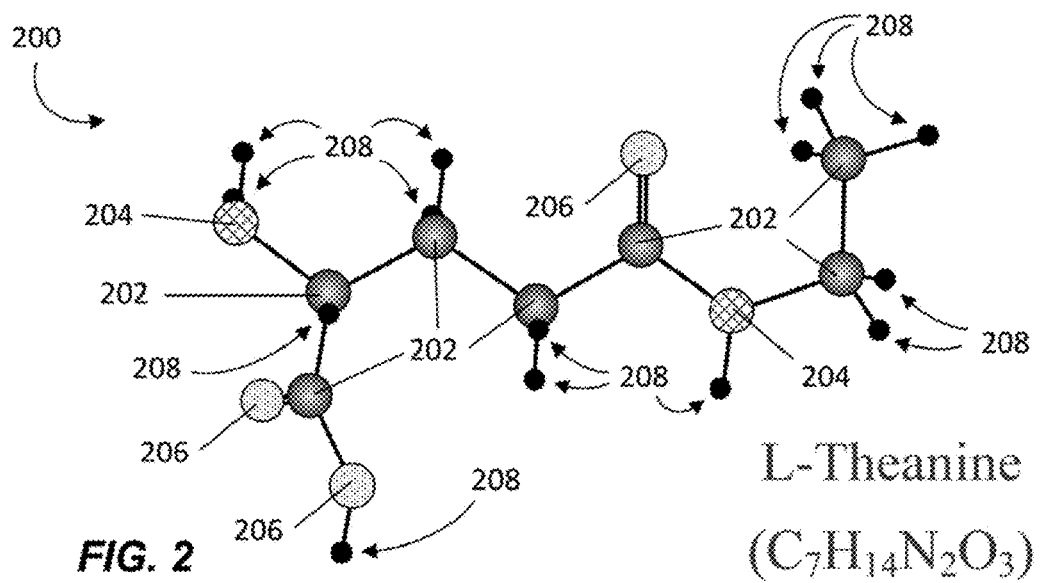
FIG. 2 is an illustration of an example of an L-theanine molecule that may be used in conjunction with the methods and compositions of the present disclosure, in accordance with one or more embodiments.

FIG. 2 is an illustration of an example of an L-theanine molecule 200 that may be used in conjunction with the methods and compositions of the present disclosure, in accordance with one or more embodiments. L-theanine, or N-Ethyl-L-glutamine, has a molecular formula $C_7H_{14}N_2O_3$. L-theanine molecule 200 includes seven Carbon atoms 202, two Nitrogen atoms 204, three Oxygen atoms 206, and fourteen Hydrogen atoms 208. L-theanine 200 is a non-protein amino acid primarily found in both green and black tea. The consumption of this nootropic has been strongly associated with a calm but alert, focused, and relatively productive (alpha wave dominant) mental state in humans.

L-theanine blocks the binding of L-glutamic acid to glutamate receptors in the brain, and inhibits cortical neuron excitation to reduce stress. At about 50 mg to 100 mg per day, L-theanine creates a sensation of focus and attentiveness, and can sharpen senses and combat fatigue. However, administration of L-theanine in greater amounts, such as above 200 mg per day or more, can have a dramatic calming effect, and excessive amounts may cause drowsiness and sedation in some individuals.

L-theanine can synergistically complement the effects of caffeine and reduce or eliminate the negative effects of caffeine consumption. Not only can the benefits of each compound be increased, but L-theanine may nullify the negative side effects of caffeine, such as hyperactive energy, darting attention span, muscle tremors, and inability to rest. In some embodiments, combining L-theanine with caffeine may also result in greater visual acuity, greater muscle dexterity, increased mental focus, improved alertness, reaction times, memory recall, and lengthened attention span.

Figure 3A:
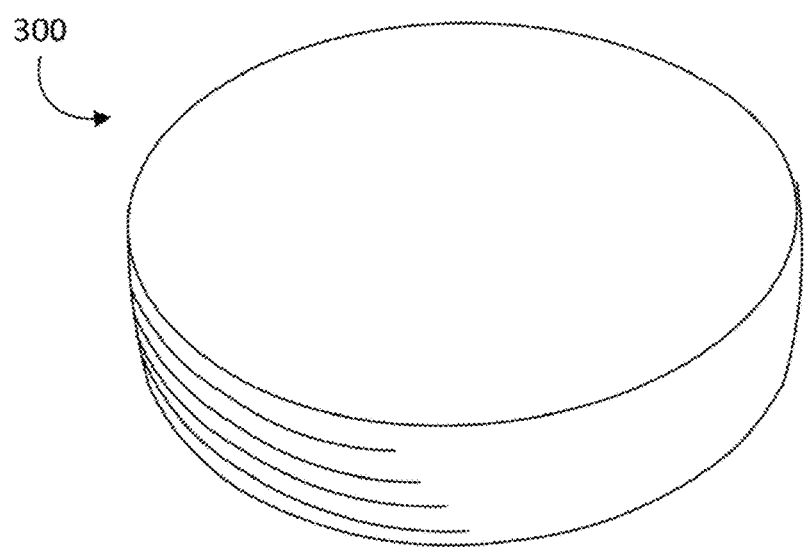
FIG. 3A illustrates an example of a nutraceutical confectionary composition in accordance with one or more embodiments of the present disclosure.
Figure 3B:
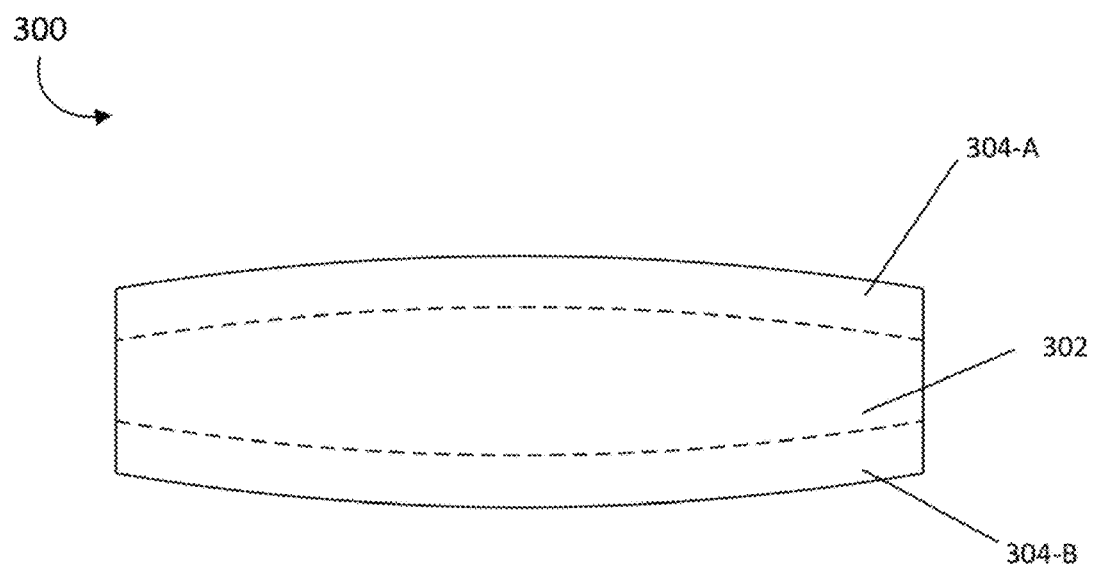
FIG. 3B illustrates another example of a nutraceutical confectionary composition with multiple layers in accordance with one or more embodiments of the present disclosure.

FIG. 3A and FIG. 3B illustrate examples of a nutraceutical confectionary composition in accordance with various embodiments of the present disclosure. According to various embodiments, a nutraceutical confectionary composition may comprise a chewing gum tablet 300 as shown in FIG. 3A. As shown in FIG. 3B, chewing gum tablet 300 may include gum base layer 302, flavor layer 304-A, and flavor layer 304-B. Each layer may include active ingredients, such as caffeine 100 and L-theanine 200. Other active ingredients may include various nootropic agents, vitamins, minerals, and probiotics.

In accordance with various embodiments, a nutraceutical confectionary composition comprising a chewing gum may be manufactured by a cold compression process. According to various embodiments, a chewing gum composition produced by cold compression format may allow for a greater consistency and potency of active ingredients in each serving. The traditional gum manufacturing process of extrusion involves high heat and moisture which may destroy or denature functional ingredients. Instead, a cold compression process avoids using heat or moisture during manufacturing operations so that the gum composition does not experience any high temperature exposures during the compression processes. By avoiding high temperatures and moisture, functional ingredients of the formulation are lost or destroyed in manufacturing, and may maintain their efficacy and potency. This allows for precise dosage calculations and consistent delivery of the functional ingredients. As a result, in some embodiments, nearly all of the active ingredients may be released into an individual's mouth by chewing.

In some embodiments, gum base, active ingredients, and inactive ingredients are provided in powdered form, combined and blended, then compressed using a pharmaceutical grade tablet press, such as a Fette press. In some embodiments, the powdered gum base may be manufactured by blending various gum base compositions through a series of mixing, drying and milling steps. In other embodiments, the gum base may be manufactured by heating and liquefying various gum base compositions to purify the gum base. The liquefied gum base is then extruded through a die to be cut into small pellets or granules, or rendered into a powder form, to be combined with other active and inactive ingredients. In a further embodiment, after the gum base is liquefied at low temperatures, the gum base may be poured into a mixer that blends the ingredients. Sweeteners, flavors, active agents, and other bioactives are added and slowly mixed in. Because of the higher temperatures involved in such embodiments, the added ingredients may be microencapsulated so as not to affect efficacy, potency, or flavoring. In some embodiments, the mixture of gum base with active and inactive ingredients are then sent to a press which stamps out circular gum pieces, such as tablet 300. In other embodiments, the gum composition may be stamped out in gum pieces of other shapes. In some embodiments, the weight of gum tablet may range from about 1000 mg to about 5000 mg.

In some embodiments, the gum pieces may be tempered by being treated at a controlled, low-temperature. In some embodiments, the gum pieces may then be fed into a spray drier that forms a hardened coating around the gum pieces. In some embodiments, the spray drier tumbles the pieces while spraying a prepared syrup mixture that is made of filtered water, sweeteners, and coloring. This combination of tumbling and spray coating forms a candy shell around the soft gum centers. In another embodiment, the hardened coating surrounding the gum pieces are added by conventional panning techniques and equipment in which one or more layers of polyol or other syrup are applied with a sprayer or ladle. Rotational motion of the panning equipment spreads the syrup and dries it into a hardened shell.

In another embodiment, gum pieces may contain multiple layers such as chewing gum tablet 300 in FIG. 3B. In some embodiments, only a gum base layer, such as gum base layer 302 in chewing gum tablet 300, may include a gum base. Such gum base may be produced through one of the processes described above. Table 1 is a representative example of the composition of a gum base layer, such as gum base layer 302.

TABLE 1

Gum Base Layer

| Ingredients | Amount (mg) | Percentage (%) |
|---|---|---|
| Gum base | 660 | 60.0000 |
| Sorbitol | 308.55 | 28.0500 |
| Natural flavors | 42.9 | 3.9000 |
| Calcium stearate | 19.8 | 1.8000 |
| Steviol glycosides | 4.4 | 0.4000 |
| Acesulfame potassium | 3.3 | 0.3000 |
| Caffeine | 20.35 | 1.8500 |
| L-theanine | 40.7 | 3.7000 |
| Gum Piece Total | Approx. 1100 mg | |

Gum base layer 302 may include both active and inactive ingredients. In various embodiments, the active ingredients may be various nootropics including stimulants, such as caffeine, and nutraceuticals, such as L-theanine, as described in FIG. 1 and FIG. 2 respectively. Other active ingredients in various embodiments may include nootropic components (such as Ashwagandha, Gotu Kola Leaf, Rosemary Leaf, Kola Nut, Cayenne, Periwinkle, *Ginseng*, Goji Berry, *Ginkgo Biloba*, Vinpocetine, Nicotine, etc.), vitamins (such as vitamin B6, vitamin B12, vitamin A, vitamin C, vitamin D, vitamin E, etc.), and minerals (such as magnesium, potassium, iron, etc.).

In various embodiments, the inactive ingredients may include flavoring agents and sweeteners such as natural flavors, sorbitol, and steviol glycosides. In some embodiments, natural flavors may include flavors such as ginger, various fruit flavors, menthol, mint, spearmint, cinnamon, etc. Sorbitol is a sweetener comprising a sugar alcohol with a sweet taste which the human body metabolizes slowly. Steviol glycosides, such as Rebaudioside A, are another sweetener comprising chemical compounds found in the leaves of the South American plant *Stevia rebaudiana* (Asteraceae). Another sweetener is acesulfame potassium which is an artificial sweetener that is stable under heat, and even under moderately acidic or basic conditions. In other embodiments, a nutraceutical confectionary composition may include various other flavoring agents and sweeteners. In some embodiments, the inactive ingredients may also include fillers, such as calcium stearate or magnesium stearate, which may also act as binding agents.

In some embodiments, flavor layers of a chewing gum tablet, such as flavor layers 304-A and 304-B, may not contain gum base. In some embodiments, a flavor layer may include a higher percentage of sweetener and flavoring. Flavor layers 304-A and 304-B may also be created by mixing powdered active and inactive ingredients and compressing the mixture in a pharmaceutical grade tablet press, such as a Fette press. Table 2 is a representative example of the composition of a flavor layer, such as flavor layer 304-A or 204-B.

TABLE 2

Flavor Layer

| Ingredients | Amount (mg) | Percentage (%) |
|---|---|---|
| Sorbitol | 257.715 | 85.9050 |
| Natural flavors | 13.332 | 4.4440 |
| Calcium stearate | 6 | 2.0000 |
| Steviol glycosides | 1.2 | 0.4000 |
| Acesulfame potassium | 1.2 | 0.4000 |
| Caffeine | 10.05 | 3.3500 |
| L-theanine | 10.20 | 3.4000 |
| Vitamin B6 | 0.3 | 0.1000 |
| Vitamin B12 | 0.003 | 0.0010 |
| Flavor Layer Total | Approx. 300 mg | |

In various embodiments, the flavor layer described by Table 2 may be flavor layer 304-A or 304-B. As described by Table 2, flavor layer 304-A or 304-B may include one or more sweeteners as previously described. In some embodiments, flavor layer 304-A or 304-B may also include one or more active ingredients as previously described. In some embodiments the pressed gum tablet 300 may be comprised of multiple instances of a gum base layer and a flavor layer. In embodiments, where one or more flavor layers form the outer layers of a gum tablet 300, the gum tablet may not undergo a coating process. In various embodiments, the weight of a gum base layer and a flavor layer may vary depending on the amounts of active and inactive ingredients included.

Figure 3C:
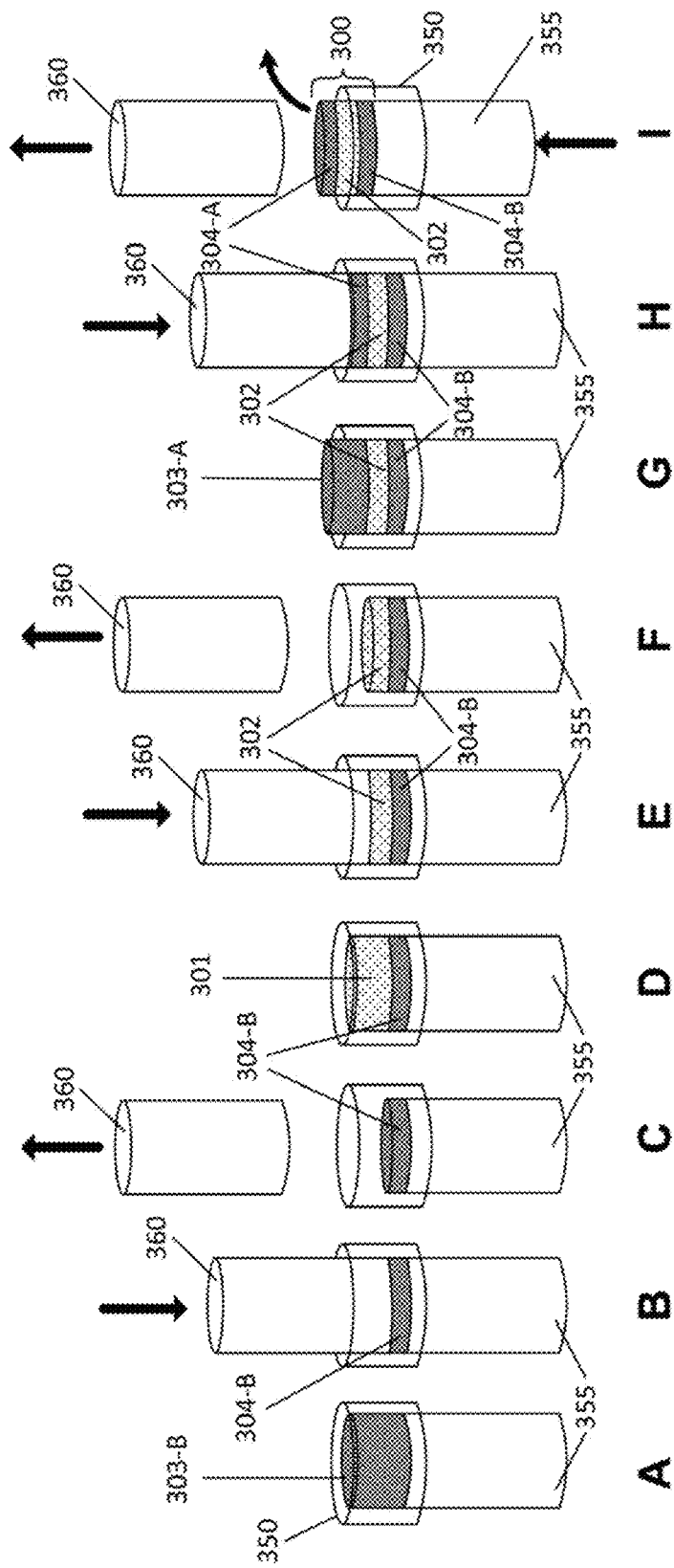
FIG. 3C illustrates an example of the formation of a multi-layer chewing gum tablet, in accordance with one or more embodiments.

FIG. 3C illustrates an example of the formation of multi-layer tablets, such as chewing gum tablet 300, in accordance with one or more embodiments. Multi-layer tablets, such as chewing gum tablet 300, may be made by compression in a pharmaceutical grade tablet press, such as a Fette press. Such press may include die 350, lower punch 355, and upper punch 360. In some embodiments, two or more different granulations or mixtures may be fed into a die in succession and compressed, one on top of another, in layers. For example, chewing gum tablet 300 is a tri-layer gum comprising three layers. A first mixture 303-B, such as the mixture described in Table 2, may be added to die 350 at step A. Mixture 303-B is then compressed between lower punch 355 and upper punch 360 at step B to form the bottom flavor layer 304-B of chewing gum tablet 300. At step C, upper punch 360 raises to allow a gum base mixture 301, such as the mixture described in Table 1, to be added to the die on top of flavor layer 304-B at step D. At step E, gum base mixture 301 is compressed on top of flavor layer 304-B to form the middle gum layer 302 of chewing gum tablet 300. At step F, upper punch 360 raises again to allow a third mixture 303-A to be added to the die on top of gum layer 302. Mixture 303-A may comprise the same or a different mixture as 303-B or 301. At step H, mixture 303-A is compressed with flavor layer 304-B and gum layer 302 to form top flavor layer 304-A of chewing gum tablet 300. Finally, at step I, upper punch 360 raises and the finished chewing gum tablet 300 may be ejected from the die by lower punch 355. This finished chewing gum tablet 300 contains three layers 302, 304-A, and 304-B and may weight approximately 1700 mg.

In other embodiments, each layer may undergo a pre-compression stage to be tamped, or packed firmly, in the die before the mixture for a successive layer is added. Once the mixture for the final layer is added into the die, the layers undergo a main compression to form chewing gum tablet 300. In various embodiments, each layer may comprise the same or different combination of active and inactive ingredients. Other embodiments may include fewer or more layers than chewing gum tablet 300 arranged in various orders. For example, a bi-layer gum tablet may be ejected at step F after mixture 301 has been compressed into gum base layer 302.

Figure 4A:
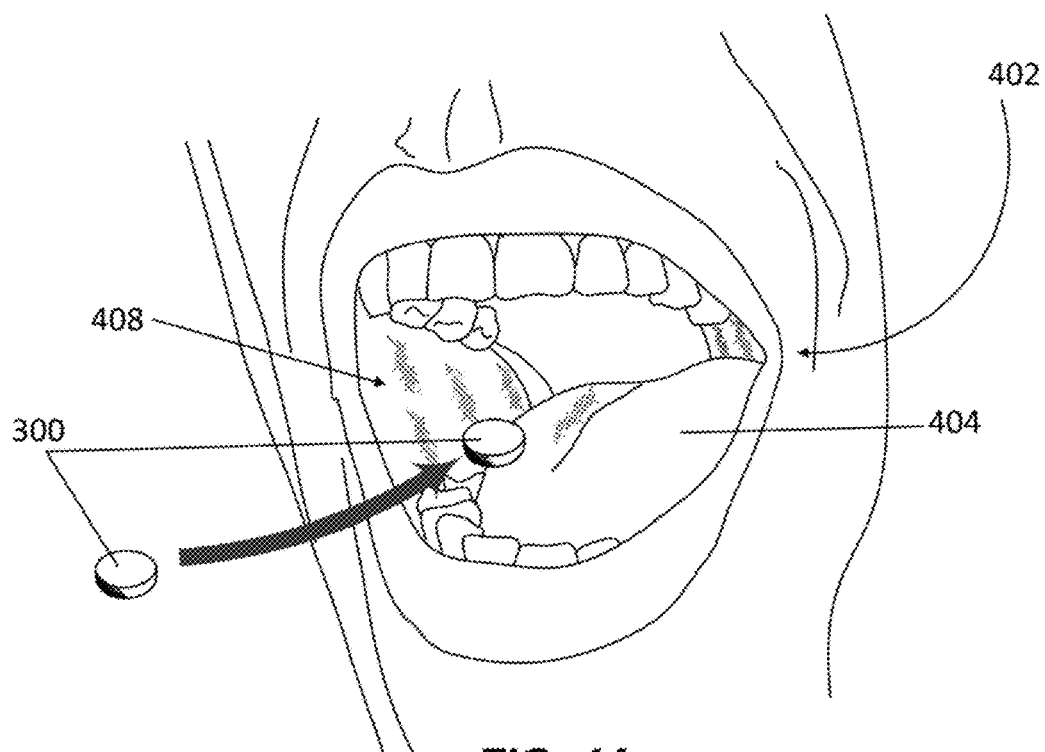
FIG. 4A illustrates the oral administration of a nutraceutical confectionary composition to an individual, in accordance with one or more embodiments.
Figure 4B:
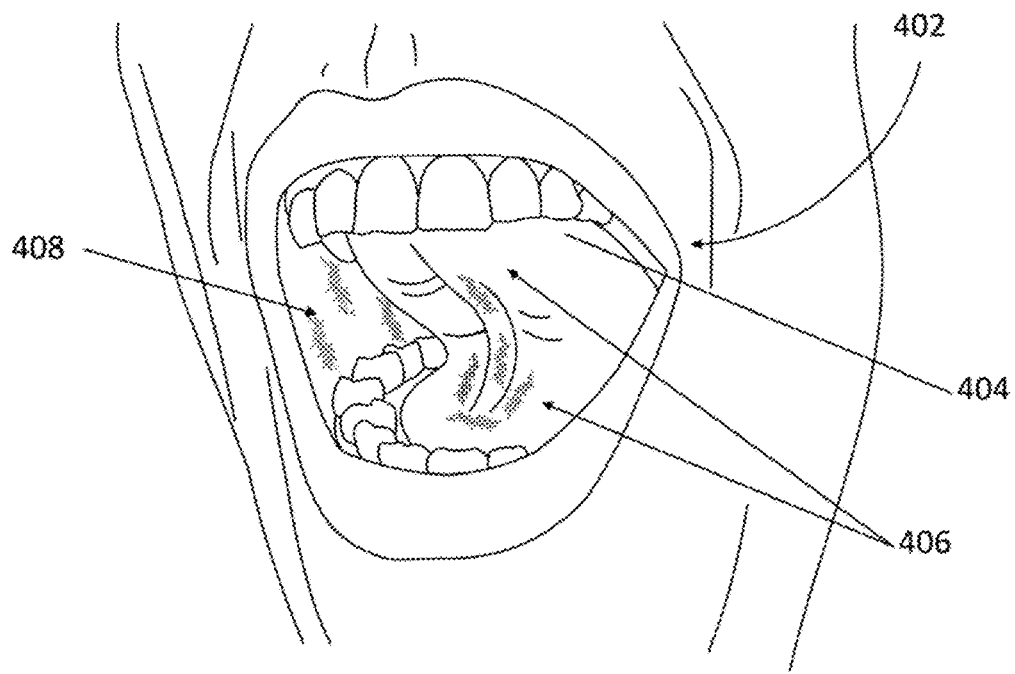
FIG. 4B illustrates the oral administration of a nutraceutical confectionary composition at the sublingual and buccal regions of an individual's oral cavity, in accordance with one or more embodiments.

According to various embodiments, the caffeine, L-theanine, and other active ingredients in a nutraceutical confectionary composition are absorbed sublingually or buccally. FIGS. 4A and 4B depict the oral administration of chewing gum tablet 300 by a user, in accordance with one or more embodiments. As described in the present disclosure, a user may place chewing gum tablet 300 in his or her oral cavity 402 to begin chewing, as shown in FIG. 4A. The size of chewing gum tablet 300 as shown in FIG. 4A is not intended as an accurate scale depiction of the size of the nutraceutical confectionary composition 300 with respect to the user's oral cavity 402.

As described in the present disclosure, absorption through the oral cavity, whether sublingually or buccally, allows for a rapid onset of action of the absorbed compounds. In some embodiments, as the subject chews gum tablet 300, active and inactive ingredients may be released from chewing gum tablet 300. In some embodiments, the released active ingredients may combine with and dissolve in the subject's saliva. In other embodiments, sucking or licking of a nutraceutical confectionary composition may cause the composition to dissolve and release the active ingredients which may mix with and dissolve in the saliva. Active ingredients, such as caffeine, L-theanine, and other vitamins and minerals, dissolved in the saliva may be absorbed at one or more sublingual regions 406 and buccal regions 408 of the subject's oral cavity 402. Sublingual region 406 comprises an area below a subject's tongue as shown in FIG. 4B. Buccal region 408 comprises regions of the oral cavity on the interior of the subject's cheeks as shown in FIGS. 4A and 4B.

A person's oral cavity is lined with a mucous membrane also known as the oral mucosa. The sublingual region 406 and buccal region 408 of the oral mucosa contain a profusion of capillaries which allow substances to be quickly absorbed into the bloodstream directly without needing to go through the digestive system. In terms of permeability, the sublingual region 406 (i.e. the floor of the mouth) is more permeable than the buccal (cheek) area 408, which is in turn is more permeable than the palatal (roof of the mouth) area. In some embodiments, sublingual and buccal administration of active ingredients keeps the active ingredients in maximum contact with the mucous membrane beneath the tongue and at the cheeks and facilitates quick diffusion into the blood vessels. Thus, active agents can make their way into the bloodstream in a matter of 30-120 seconds and onto the brain directly. Consequently, the desired effects (i.e., increase in focus, alleviation of fatigue, enhancement of mental clarity, improvement of nervous system functions, reduction of stress, and decrease in anxiety) can be experienced strongly, and almost immediately.

Sublingual and buccal administration has certain advantages over typical oral administration involving swallowing. Being more direct, it is often faster, and it ensures that the substance will risk degradation only by salivary enzymes before entering the bloodstream. This may ensure that nearly all of the active ingredients released by chewing gum tablet 300 to be absorbed quickly into the bloodstream and allow a lower dose to be included in a nutraceutical confectionary composition. In some embodiments, peak plasma levels of active ingredients may be reached in an individual within 1 to 2 minutes. In contrast, administering active agents through oral ingestion is a time consuming process and may require up to an hour or longer for active ingredients, such as caffeine and L-theanine, to pass through the digestive tract to be absorbed by the small intestine. It may take even more time for the active agents to make their way into the bloodstream and for any effect to be felt. Additionally, administration of a larger amount of active ingredients may be required through oral ingestion because orally ingested substances must survive passage through the hostile environment of the gastrointestinal tract after being swallowed, risking degradation of the substance, either by stomach acid or bile, or by the many enzymes therein. Furthermore, after absorption from the gastrointestinal tract, such drugs must pass to the liver before entering general circulation of the bloodstream, where they may be extensively altered; this is known as the "first pass effect" of drug metabolism. Due to the digestive activity of the stomach and intestines and the solubility of the GI tract, the oral route may be unsuitable for certain substances and/or compounds.

In some embodiments, sublingual or buccal administration of caffeine by chewing a chewing gum tablet 300 may avoid certain negative effects of consuming more traditional sources of caffeine, such as halitosis, stained teeth, and other gastrointestinal issues. Pigments from dark-colored drinks, such as coffee, tea, and soda, can become embedded in microscopic pits and ridges in tooth enamel causing yellowing stains which can be permanent. Drinking coffee may also be more likely to cause halitosis by the user because coffee includes a strong odor and contains sulfurous content which certain odor-causing bacteria can break down to produce odor. Additionally, coffee contains various oils, acids and compounds that may harm your stomach and intestines by irritating the gastrointestinal linings. Coffee may also stimulate peristalsis in the gastrointestinal tract and cause emptying of the stomach contents before proper digestion. In some embodiments, direct absorption of caffeine through sublingual or buccal administration may avoid such negative effects. In other embodiments, the act of chewing gum may also increase alertness and concentration, and may also provide advantages complementary to the synergistic effects of caffeine and L-theanine. Chewing gum may also be a pleasurable activity for an individual.

A representative serving of a nutraceutical confectionary composition of chewing gum may include the following ingredients of Table 3.

TABLE 3

| Ingredients | Range (mg) |
| --- | --- |
| Sorbitol | 600-900 |
| Gum base | 600-700 |
| Natural flavors | 20-100 |
| Calcium stearate | 20-50 |
| Steviol glycosides | 5.0-7.5 |
| Acesulfame potassium | 4.5-7.0 |
| Caffeine | 40-100 |
| L-theanine | 40-200 |
| Vitamin B6 | 0.3-1.0 |
| Vitamin B12 | 0.0050-0.0080 |
| Gum Piece Total | Approx. 1334-3401 mg |

As shown in Table 3, a representative serving of a nutraceutical confectionary composition of chewing gum may range in size from approximately 1334 mg to approximately 3400 mg. In other embodiments, a chewing gum may weigh as low as 1000 mg. In various embodiments, the weight of a chewing gum tablet may vary depending on the amounts of sweeteners, flavoring, and gum base included. In other embodiments, the weight of a chewing gum tablet may vary depending on the amounts of active ingredients included, such as caffeine, L-theanine, vitamin B6, and vitamin B12. In some embodiments, a chewing gum tablet can weigh up to 5000 mg. In an embodiment with increased the amounts of gum base may allow increased amounts of flavoring agents and sweeteners to be included. As a result, the taste and flavor of the gum tablet may last longer because such ingredients may be released more slowly as chewing is required to release the flavoring agents and sweeteners. In such embodiments, active ingredients, such as caffeine and L-theanine, may also be released more slowly because more chewing is required to release the active ingredients.

A typical cup of coffee may contain approximately 50 mg to 200 mg of caffeine. Administering about 40 mg to about 100 mg of caffeine to a subject per serving would provide the subject with an amount of caffeine in about half a typical cup or less of coffee and may allow a user to better select incremental amounts of caffeine to administer. In some embodiments, the amount of L-theanine in the individual should be equal or higher than that of caffeine in order for the individual to experience optimal synergistic effects of the combination of caffeine and L-theanine. Where the amount of L-theanine is lower than that of caffeine, the L-theanine may not be able to offset the negative side effects of caffeine, such as hyperactive energy, darting attention span, muscle tremors, and inability to rest.

The elimination half-life (denoted $t_{1/2}$) of a substance, such as caffeine or L-theanine, is the time it takes for the substance to lose half of its pharmacologic activity. The amount of a substance in an individual may be determined by the elimination half-life with the following equation:

$$C_t = C_0 e^{-kt}$$

In the equation above, $C_t$ is the concentration at time r, $C_0$ is the initial concentration, and k is the elimination constant, given by $k = \log(2)/t_{1/2}$. The elimination half-life of a substance may vary among individual humans, but the elimination half-life of L-theanine has been shown to be faster than that of caffeine. The elimination half-life of L-theanine in an adult human body may be in the range from 1 to 2 hours, while the elimination of half-life of caffeine in an adult human body may be in the range from 4 to 6 hours. In other individuals, the half-life of caffeine has been measured to be as fast as 3 hours to as slow as 7 hours. With these elimination half-lives, in some embodiments, the amount of L-theanine will decrease faster than the amount of caffeine in a subject who has been administered the nutraceutical confectionary composition. Thus, the initial amount of L-theanine in the confectionary composition must be greater, than or equal to, the initial amount of caffeine in order to sustain optimal synergistic effects for a desired time. In some embodiments, the nutraceutical confectionary may contain a ratio of caffeine to L-theanine of about 2:3. With two parts caffeine to three parts L-theanine, the amount of L-theanine may exceed the amount of caffeine in the subject for about 40 minutes to about 140 minutes, and providing the subject with optimal synergistic effects for such time.

FIGS. 6A-6F illustrate graphical representations of the amounts of active ingredients present in an individual over time upon administration of a nutraceutical confectionary composition, in accordance with one or more embodiments. For example, a nutraceutical confectionary composition may contain caffeine and L-theanine in about a 2:3 ratio with approximately 40 mg of caffeine and approximately 60 mg of L-theanine. With reference to FIGS. 6A-6D, graphs 600-A, 600-B, 600-C, and 600-D are presented to show the amounts of active ingredients that may be present in an individual over time after administration of a nutraceutical confectionary composition that contains caffeine and L-theanine in about a 2:3 ratio, given varying elimination half-lives. Graphs 600-A, 600-B, 600-C, and 600-D assume that all of the active ingredients released by the nutraceutical confectionary composition have been rapidly absorbed by the individual's oral mucosa and that the peak plasma levels for each active ingredient have been reached. For example, a particular individual, L-theanine may have a half-life of 1 hour and caffeine may have a half-life of 6 hours, as depicted by Graph 600-A in FIG. 6A.

In Graph 600-A, line 601-A represents the amount of caffeine over time beginning at about 40 mg, line 602-A represents the amount of L-theanine over time beginning at about 60 mg, and line 603-A marks the point at which the amount of caffeine may equals the amount of L-theanine. Graph 600-A shows that with the given half-lives at about a 2:3 ratio, L-theanine will be present at a higher concentration than caffeine in the particular person for about 42 to 43 minutes.

In another particular individual, L-theanine may have a half-life of 2 hours and caffeine may have a half-life of 6 hours. Graph 600-B shows the amounts of active ingredients that may be present in a person over time after administration of a nutraceutical confectionary composition containing caffeine and L-theanine in about a 2:3 ratio given such elimination half-lives.

In Graph 600-B, line 601-B represents the amount of caffeine over time beginning at about 40 mg, line 602-B represents the amount of L-theanine over time beginning at about 60 mg, and line 603-B marks the point at which the amount of caffeine may equals the amount of L-theanine. Graph 600-B shows that with the given half-lives at about a 2:3 ratio, L-theanine will be present at a higher concentration than caffeine in the particular person for about 105 to 106 minutes.

In another particular individual, L-theanine may have a half-life of 1 hour and caffeine may have a half-life of 4 hours. Graph 600-C shows the amounts of active ingredients that may be present in a person over time after administration of a nutraceutical confectionary composition containing caffeine and L-theanine in about a 2:3 ratio given such elimination half-lives.

In Graph 600-C, line 601-C represents the amount of caffeine over time beginning at about 40 mg, line 602-C represents the amount of L-theanine over time beginning at about 60 mg, and line 603-C marks the point at which the amount of caffeine may equals the amount of L-theanine. Graph 600-C shows that with the given half-lives at about a 2:3 ratio, L-theanine will be present at a higher concentration than caffeine in the particular person for about 46 to 47 minutes.

In another particular individual, L-theanine may have a half-life of 2 hours and caffeine may have a half-life of 4 hours. Graph 600-D shows the amounts of active ingredients that may be present in a person over time after administration of a nutraceutical confectionary composition containing caffeine and L-theanine in about a 2:3 ratio given such elimination half-lives.

In Graph 600-D, line 601-D represents the amount of caffeine over time beginning at about 40 mg, line 602-D represents the amount of L-theanine over time beginning at about 60 mg, and line 603-D marks the point at which the amount of caffeine may equals the amount of L-theanine. Graph 600-D shows that with the given half-lives at about a 2:3 ratio, L-theanine will be present at a higher concentration than caffeine in the particular person for about 140 to 141 minutes.

Graphs 600-A, 600-B, 600-C, and 600-D show that with two parts caffeine to three parts L-theanine, the amount of L-theanine may exceed the amount of caffeine in various individuals for approximately 40 minutes to 110 minutes with varying elimination half-lives. In such embodiments, a nutraceutical confectionary composition may provide the subject with optimal synergistic effects for such time that the concentration of L-theanine exceeds the concentration of caffeine.

Example 1

A representative serving of nutraceutical confectionary composition of chewing gum may include the following ingredients of Table 4.

TABLE 4

Chewing Gum Composition Example 1

| Ingredients | Amount (mg) | Percentage (%) |
| --- | --- | --- |
| Sorbitol | 823.98 | 48.5 |
| Gum base | 660 | 38.8 |
| Natural flavors | 61.064 | 3.59 |
| Calcium stearate | 31.8 | 1.87 |
| Natural Menthol | 8.5 | 0.5 |
| Steviol glycosides | 6.8 | 0.4 |
| Acesulfame potassium | 5.7 | 0.33 |
| Caffeine | 40.45 | 2.38 |
| L-theanine | 61.1 | 3.59 |
| Vitamin B6 | 0.6 | 0.04 |
| Vitamin B12 | 0.0060 | 0.00035 |
| Flavor Layer Total | Appxox. 1700 mg | 100 |

The chewing gum composition of Example 1 is approximately 1700 mg and contains caffeine and L-theanine in approximately a 2:3 ratio with approximately 40 mg of caffeine and approximately 60 mg of L-theanine.

Example 2

In various embodiments, the nutraceutical confectionary may contain caffeine and L-theanine in a ratio ranging from 1:1 to 1:2. In some embodiments, the amount of caffeine in the confectionary may range from 5 mg per serving to 100 mg per serving. In some embodiments, the amount of L-theanine in the confectionary may range from 5 mg per serving to 200 mg per serving. Another representative serving of a chewing gum may comprise a 4:5 ratio of about 100 mg caffeine to about 125 mg L-theanine. Providing about 100 mg of caffeine may provide an individual with about as much caffeine as a typical cup of coffee. Providing four parts caffeine to five parts L-theanine will provide more caffeine relative to L-theanine as compared to the chewing gum composition described in Example 1. As such, the effects of caffeine will be nullified to a lesser degree. Taking into account elimination half-life ranges of the substances, the amount of L-theanine may exceed the amount of caffeine in the subject for about 20 minutes to about 80 minutes, and providing the subject with optimal synergistic effects for such time.

Figure 6A:
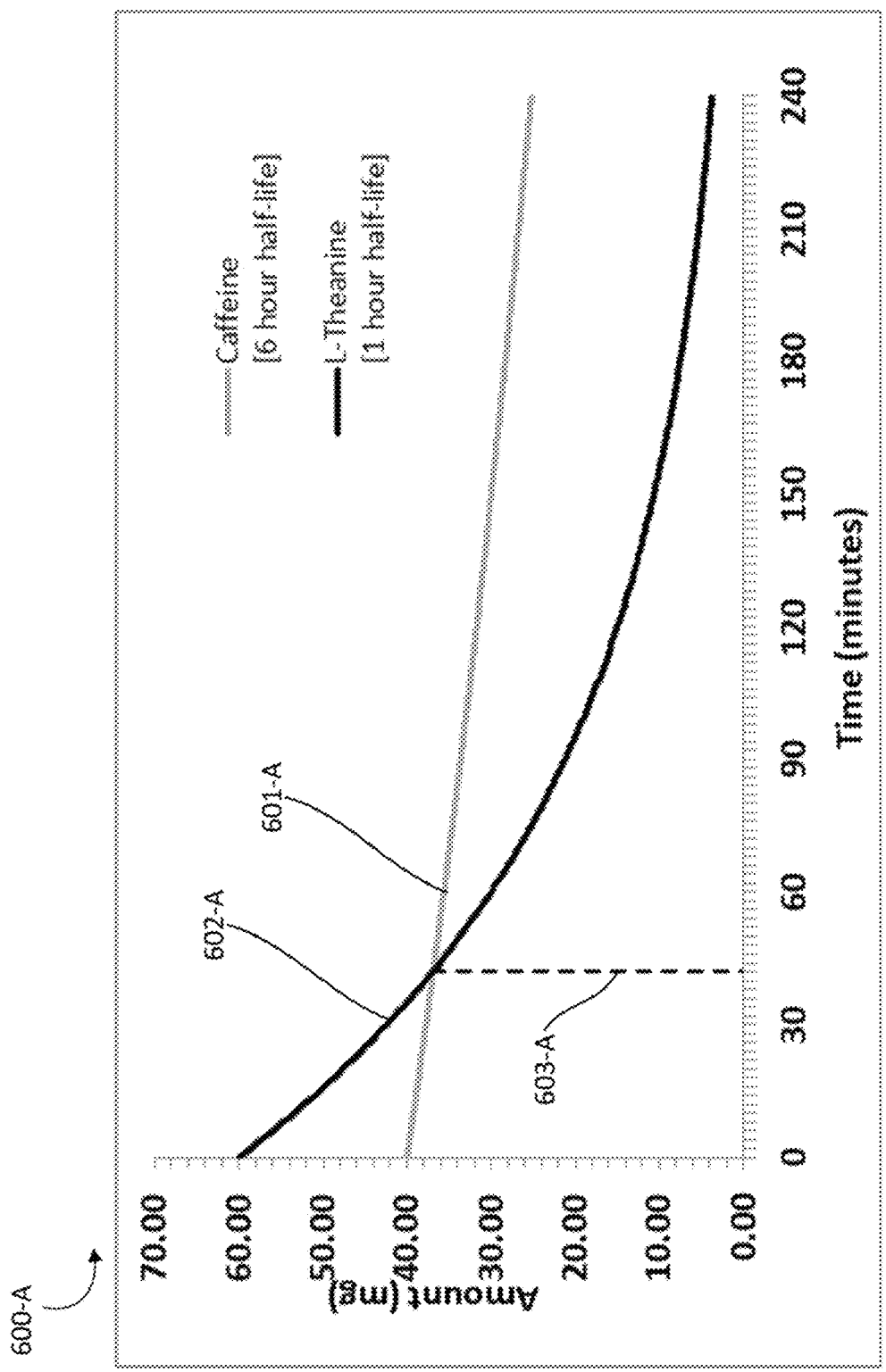
FIGS. 6A-6F illustrate graphical representations of the amounts of active ingredients present in an individual over time upon administration of a nutraceutical confectionary composition, in accordance with one or more embodiments.
Figure 6B:
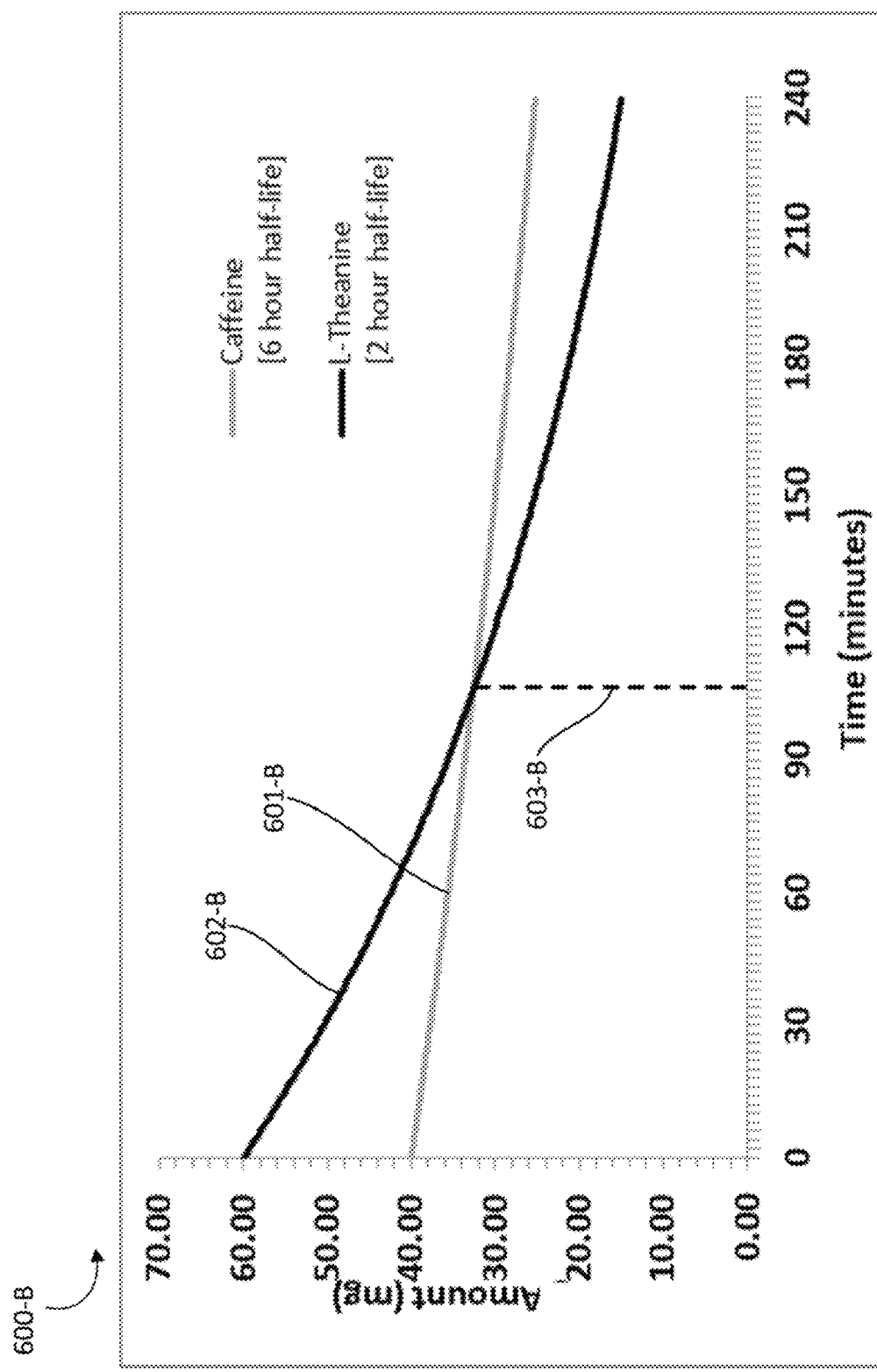
Figure 6C:
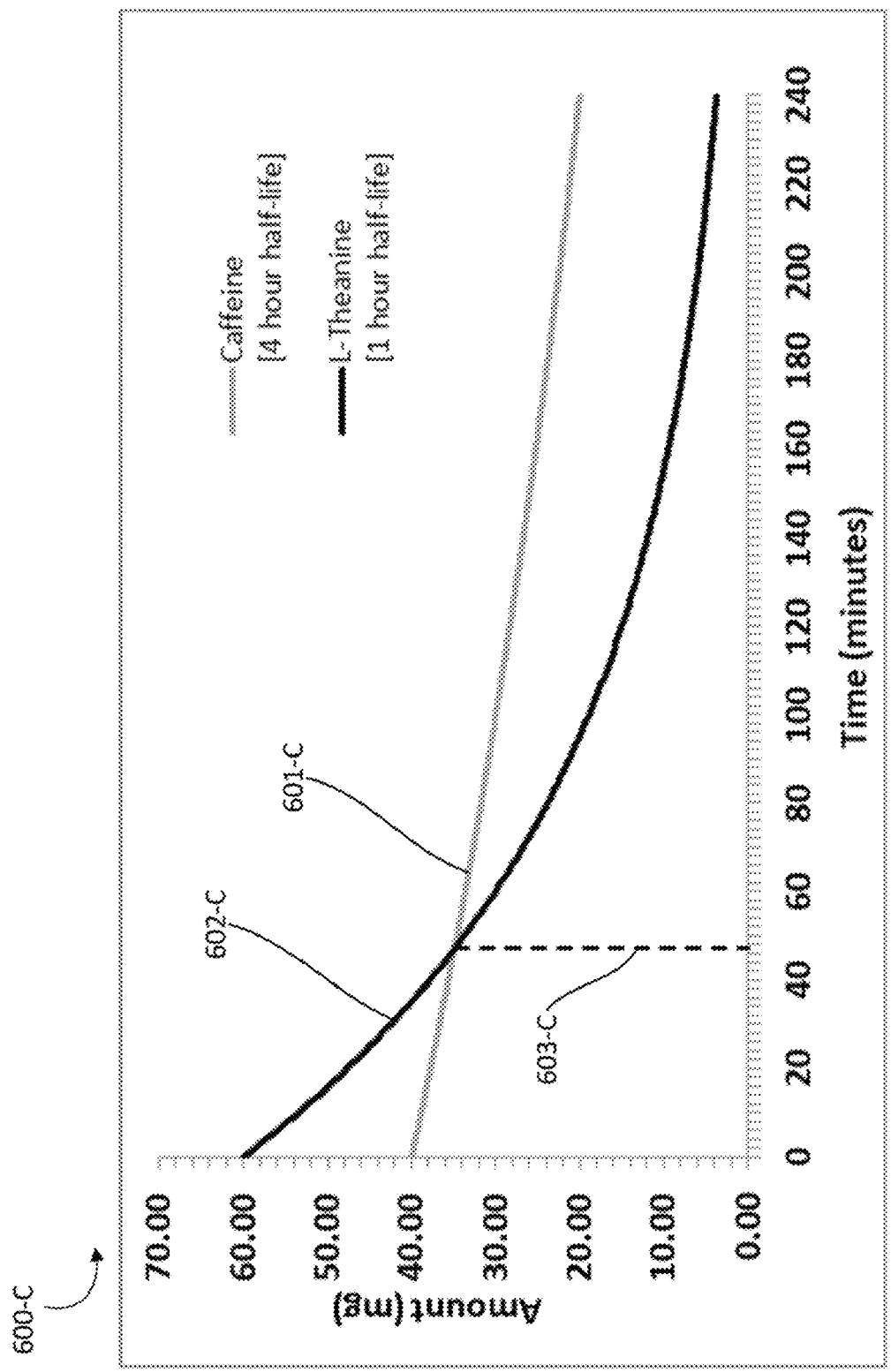
Figure 6D:
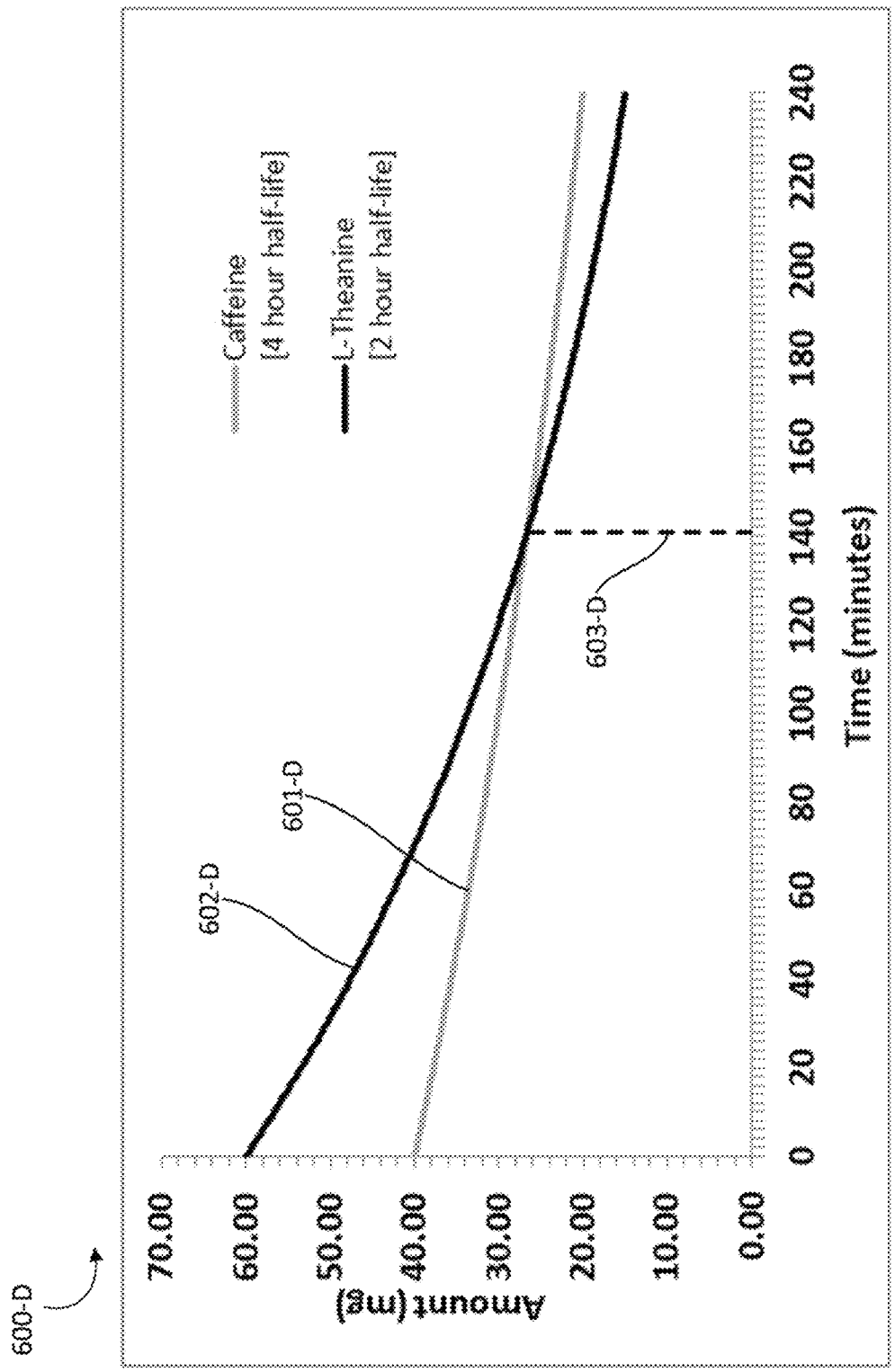
Figure 6E:
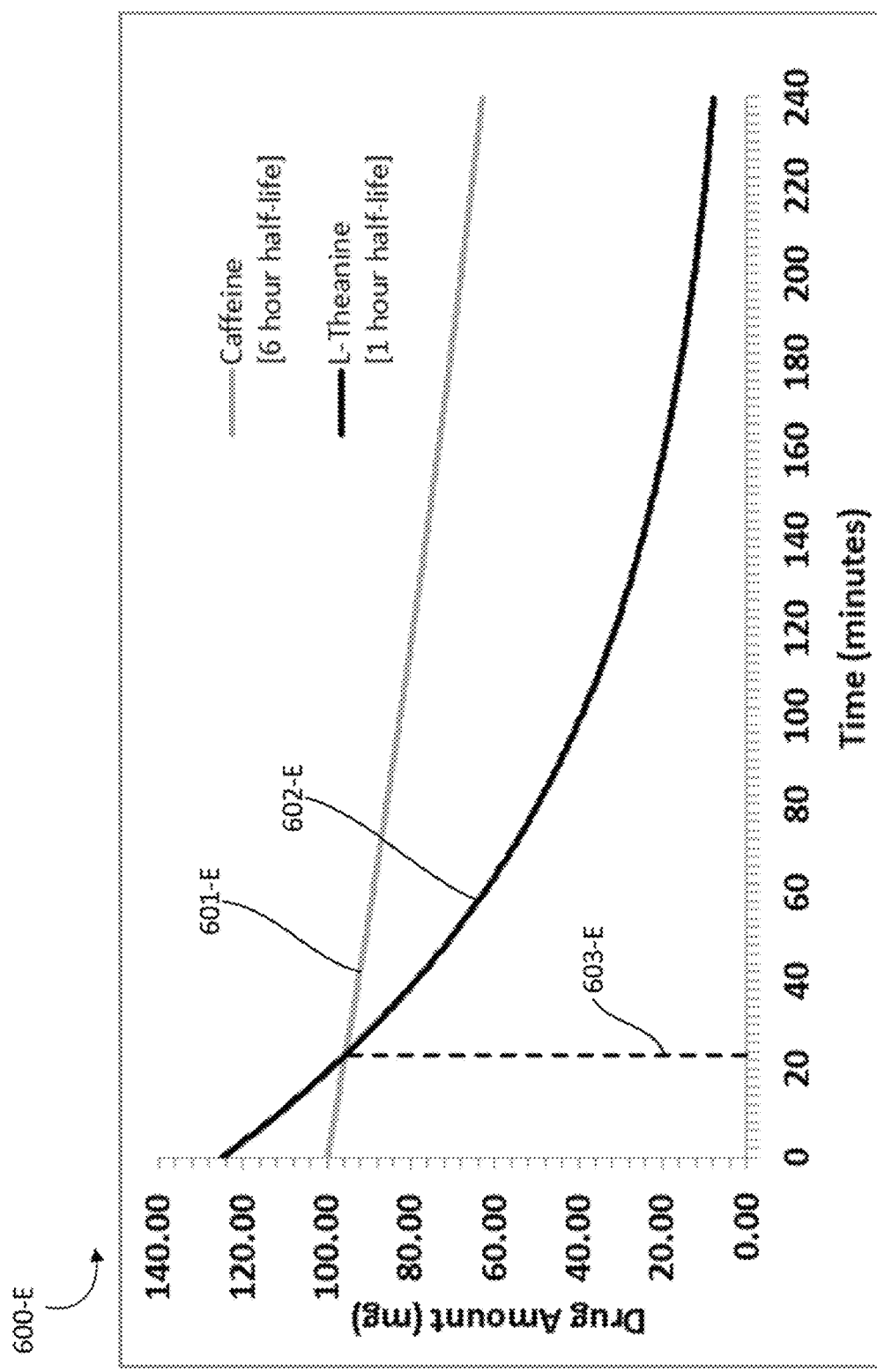
Figure 6F:
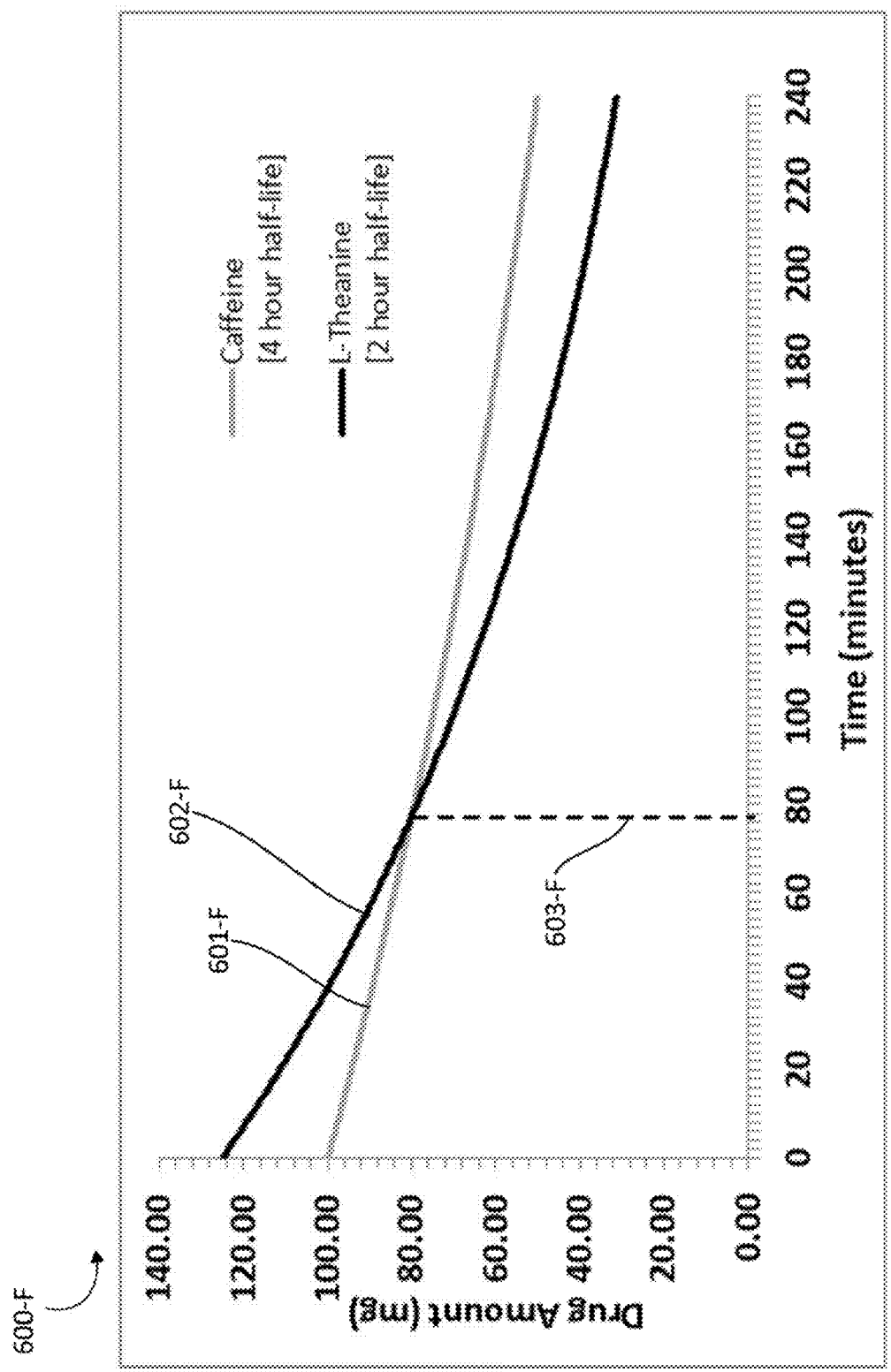

With reference to FIGS. 6E-6F, Graph 600-E in FIG. 6E and Graph 600-F in FIG. 6F show the amounts of active ingredients that may be present in a person over time after administration of a nutraceutical confectionary composition containing caffeine and L-theanine in about a 4:5 ratio given possible elimination half-lives. Graphs 600-E and 600-F assume that all of the active ingredients released by the nutraceutical confectionary composition have been rapidly absorbed by the individual's oral mucosa and that the peak plasma levels for each active ingredient have been reached.

Graph 600-E shows the amounts of caffeine and L-theanine in a particular individual in which L-theanine may have a half-life of 1 hour and in which caffeine may have a half-life of 6 hours. In Graph 600-E, line 601-E represents the amount of caffeine over time beginning at about 100 mg, line 602-E represents the amount of L-theanine over time beginning at about 125 mg, and line 603-E marks the point at which the amount of caffeine may equals the amount of L-theanine. In such an individual, L-theanine may be present at a higher concentration than caffeine in the particular person for about 23 minutes to 24 minutes. Graph 600-F shows the amounts of caffeine and L-theanine in a particular individual in which L-theanine may have a half-life of 2 hour and in which caffeine may have a half-life of 4 hours. In Graph 600-F, line 601-F represents the amount of caffeine over time beginning at about 100 mg, line 602-F represents the amount of L-theanine over time beginning at about 125 mg, and line 603-F marks the point at which the amount of caffeine may equals the amount of L-theanine. In such an individual, L-theanine may be present at a higher concentration than caffeine in the particular person for about 77 minutes to 78 minutes. Graphs 600-E and 600-F show that with four parts caffeine to five parts L-theanine, the amount of L-theanine may exceed the amount of caffeine in various individuals for approximately 20 minutes to approximately 80 minutes with varying elimination half-lives.

In some embodiments, a gum composition, such as chewing gum tablet 300, may include increased amounts of gum base. For example, a gum composition may include about 1000 mg to about 1500 mg of gum base. As previously described, in such heavier gum compositions with more gum base, active ingredients may be released more slowly because more chewing is required to release the active ingredients mixed within the gum base. Similarly, some embodiments of a nutraceutical confectionary composition may be a hard candy which may dissolve over a longer time period, such as 15 to 20 minutes, in an individual's oral cavity. Where active ingredients are released in such a slow, delayed fashion, the relative amount of L-theanine may be lowered. For example, the ratio of caffeine to L-theanine may be about 4:5 to about 1:1. In such embodiments, the equal or greater amount of L-theanine is maintained in the individual because the active ingredients may be continuously released in the desired ratio, and continually absorbed by the individual's oral mucosa in the desired ratio.

In other embodiments, a flavor layer, such as 304-A and 304-B, that forms an outer layer of a chewing gum tablet, may dissolve faster and the ingredients within the flavor layer may be absorbed by the individual before the ingredients mixed within the gum base layer, which require more chewing to release. In such embodiments, an outer flavor layer may include a higher ratio of caffeine to L-theanine such that there is an equal or larger amount of caffeine relative to the amount of L-theanine. In some embodiments, an outer flavor layer may include only caffeine and no L-theanine. In other embodiments, the gum base layer, such as gum base layer 302, may include only L-theanine and no caffeine. An individual would receive a higher amount of caffeine initially and experience the effects of caffeine as the flavor layer dissolves and is absorbed first. As the individual continues to chew the gum composition, L-theanine may be released and absorbed such that L-theanine is present in the individual in a larger amount than caffeine.

In further embodiments, L-theanine may be absorbed more slowly than caffeine by an individual's oral cavity. In other embodiments, L-theanine may be released more slowly than caffeine where there is an increased amount of gum base. In such embodiments, the concentration of caffeine in the individual will rise faster than that of L-theanine if the two active ingredients are provided in a 1:1 ratio. In such embodiments, the relative amount of L-theanine to caffeine may be increased such that the ratio of caffeine to L-theanine may range from about 3:5 to about 1:2. A higher concentration of L-theanine in the gum formulation would ensure that the L-theanine concentration within the individual remains equal to or higher than that of caffeine despite slower release or absorption rate.

Figure 5:
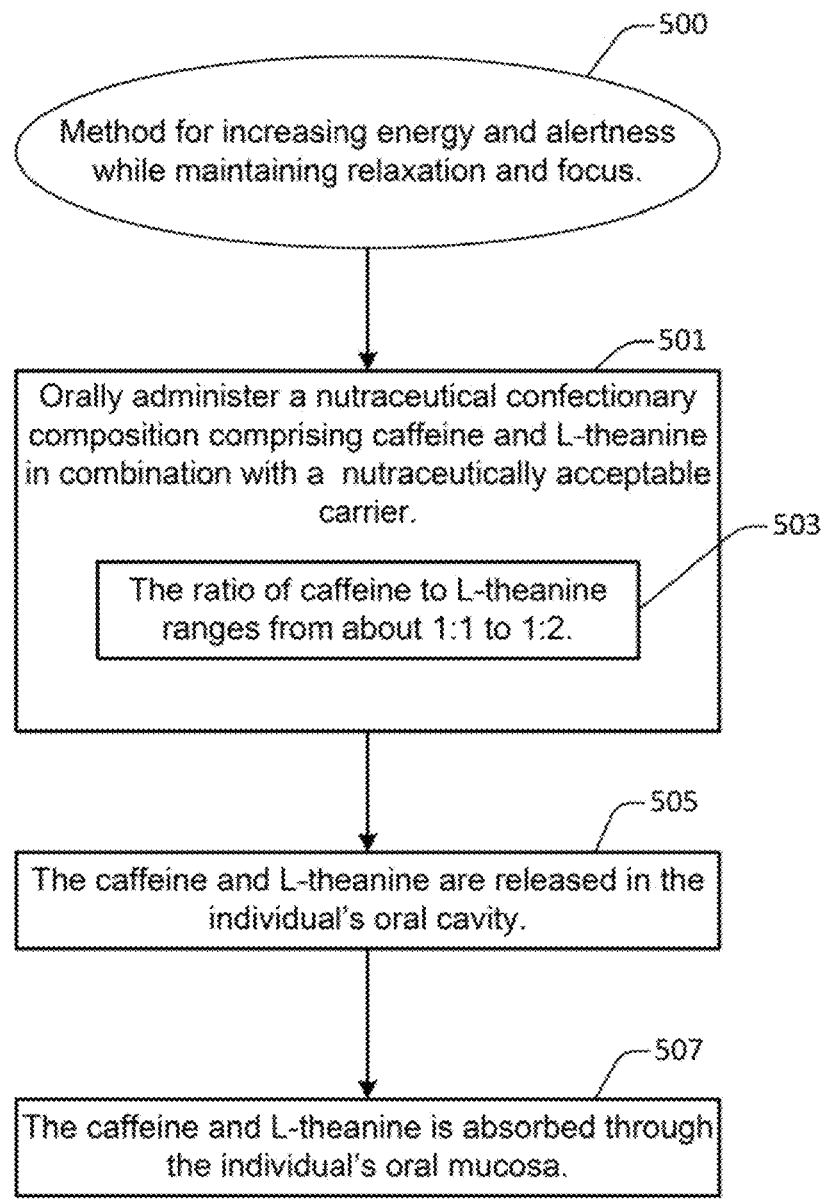
FIG. 5 illustrates an example of a method for treating a subject for increasing energy and alertness while maintaining relaxation and focus, in accordance with one or more embodiments.

FIG. 5 illustrates an example of a method 500 for treating a subject for increasing energy and alertness while maintaining relaxation and focus, in accordance with one or more embodiments. Method 500 comprises a step 501 of orally administering to an individual a nutraceutical confectionary composition comprising caffeine and L-theanine in combination with a nutraceutically acceptable carrier. In some embodiments, the nutraceutical confectionary composition may be placed in the individual's oral cavity. In some embodiments, the nutraceutical confectionary composition may comprise a chewing gum such as chewing gum tablet 300, in which the nutraceutically acceptable carrier includes a gum base. Such chewing gum tablet 300 may be manufactured as described in FIGS. 3B and 3C. In other embodiments, the nutraceutical confectionary composition may comprise other confectionaries, such as mints, hard candies, soft candies, dissolvable strips, baked goods, liquid drops, liquid sprays, etc. The nutraceutical confectionary composition includes a ratio 503 of caffeine to L-theanine that ranges from about 1:1 to 1:2. For example chewing gum tablet 300, as described in FIGS. 3A, 3B, and 3C may include a 2:3 ratio of caffeine to L-theanine. The chewing gum tablet 300 may comprise about 40 mg of caffeine and about 60 mg of L-theanine as described in Table 4. According to various embodiments, the nutraceutical confectionary composition may include other active nootropic ingredients as previously described in FIGS. 3A, 3B, and 3C. According to various embodiments, the nutraceutical confectionary composition may include other inactive ingredients as previously described in FIGS. 3A, 3B, and 3C.

At 505, the caffeine and L-theanine are released in the individual's oral cavity. In some embodiments, the nutraceutical confectionary composition remains in the mouth to be chewed or dissolved such that the caffeine and L-theanine are released in the individual's oral cavity and dissolved in the individual's saliva. For example, chewing gum tablet 300 may be chewed by the individual, as described in FIGS. 4A and 4B, releasing the active ingredients of caffeine and L-theanine. In other embodiments, other active and inactive ingredients, as previously described, may also be released in the individual's oral cavity.

According to various embodiments, the active ingredients, including caffeine and L-theanine, are dissolved in the individual's saliva and are absorbed through the individual's oral mucosa at step 507. In some embodiments, the active ingredients may come into contact with sublingual and/or buccal regions of the oral mucosa, which include a profusion of capillaries that quickly absorb the active ingredients directly into the bloodstream. Once in the bloodstream, the caffeine and L-theanine may act synergistically to provide several beneficial effects. In various embodiments, such beneficial effects may include increased focus and attentiveness, sharpened senses, elimination of fatigue. In addition, the L-theanine may nullify the negative side effects of caffeine, such as hyperactive energy, darting attention span, muscle tremors, and inability to rest.

While the present disclosure has been particularly shown and described with reference to specific embodiments thereof, it will be understood by those skilled in the art that changes in the form and details of the disclosed embodiments may be made without departing from the spirit or scope of the present disclosure. It is therefore intended that the present disclosure be interpreted to include all variations and equivalents that fall within the true spirit and scope of the present disclosure. Although many of the components and processes are described above in the singular for convenience, it will be appreciated by one of skill in the art that multiple components and repeated ingredients can also be used to form the compositions of the present disclosure.

What is claimed is:

1. A chewing gum consisting of:
    a gum base layer consisting of:
        gum base in an amount of approximately 660.0 mg,
        sorbitol in an amount of approximately 308.55 mg,
        natural flavors in an amount of approximately 42.9 mg,
        calcium stearate in an amount of approximately 19.8 mg,
        steviol glycosides in an amount of approximately 4.4 mg,
        acesulfame potassium in an amount of approximately 3.3 mg,
        caffeine in an amount of approximately 20.35 mg, and
        L-theanine, in an amount of approximately 40.7 mg; and
    a first flavor layer and a second flavor layer, each flavor layer consisting of:
        sorbitol in an amount of approximately 257.7 mg,
        natural flavors in an amount of approximately 13.3 mg,
        calcium stearate in an amount of approximately 6.0 mg,
        steviol glycosides in an amount of approximately 1.2 mg,
        acesulfame potassium in an amount of approximately 1.2 mg,
        Vitamin B6 in an amount of approximately 0.3 mg,
        Vitamin B12 in an amount of approximately 0.003 mg,
        caffeine in an amount of approximately 10.05 mg, and
        L-theanine in an amount of approximately 10.20 mg;
    wherein the gum base layer is positioned in between the first flavor layer and the second flavor layer.

2. The composition of claim 1, wherein the chewing gum is a tablet manufactured by a process comprising:
    (a) providing the gum base as a powdered gum base;
    (b) forming a first mixture by combining the gum base with caffeine, L-theanine, sorbitol, natural flavors, calcium stearate, steviol glycosides, and acesulfame potassium;
    (c) forming a second mixture by combining caffeine, L-theanine, sorbitol, natural flavors, calcium stearate, steviol glycosides, acesulfame potassium, Vitamin B6, and Vitamin B12;
    (d) loading a first serving of the second mixture into a die in a tablet compression system;
    (e) compressing the first serving of the second mixture into the first flavor layer of the tablet;
    (f) loading a serving of the first mixture into the die, wherein the serving of the first mixture is loaded onto the first flavor layer;
    (g) compressing the serving of the first mixture into the gum base layer of the tablet coupled to the first flavor layer;
    (h) loading a second serving of the second mixture into the die, wherein the second serving of the second mixture is loaded onto the gum base layer;
    (i) compressing the second serving of the second mixture into the second flavor layer of the tablet—coupled to the—gum base layer; and
    (j) ejecting the tablet from the die.

3. A method for increasing energy and alertness while maintaining relaxation and focus, the method comprising:
    orally administering to an individual the chewing gum of claim 1.

4. The method of claim 3, wherein chewing of the chewing gum by the individual causes the caffeine and L-theanine to be released into the individual's oral cavity.

5. The method of claim 3, wherein the chewing gum further consists of one or more vitamins or minerals.

* * * * *